United States Patent [19]
Burns

[11] Patent Number: 5,494,170
[45] Date of Patent: Feb. 27, 1996

[54] COMBINATION STOPPER-SHIELD CLOSURE

[75] Inventor: James A. Burns, Elizabeth, N.J.

[73] Assignee: Becton Dickinson and Company, Franklin Lakes, N.J.

[21] Appl. No.: 58,854

[22] Filed: May 6, 1993

[51] Int. Cl.⁶ .................................. B65D 41/50
[52] U.S. Cl. ................ 215/247; 215/251; 215/249
[58] Field of Search ........................ 215/247, 249, 215/251; 604/415, 403

[56] References Cited

U.S. PATENT DOCUMENTS

| | | | |
|---|---|---|---|
| 3,193,128 | 7/1965 | Ravn | 215/249 |
| 3,358,865 | 12/1967 | Andersen | 215/249 |
| 4,205,754 | 6/1980 | Nielsen et al. | 215/251 |
| 4,465,200 | 8/1984 | Percarpio | 215/247 |
| 4,478,342 | 10/1984 | Slater et al. | 215/251 |
| 4,967,919 | 11/1990 | Earhart | 215/247 |
| 5,038,951 | 8/1991 | Rizzardi | 215/251 |
| 5,143,236 | 9/1992 | Gueret | 215/249 |
| 5,232,111 | 8/1993 | Burns | 215/247 |
| 5,275,299 | 1/1994 | Konrad et al. | 215/247 |
| 5,294,011 | 3/1994 | Konrad et al. | 215/247 |
| 5,303,835 | 4/1994 | Haber et al. | 215/247 |
| 5,314,084 | 5/1994 | Folta et al. | 215/251 |
| 5,335,801 | 8/1994 | Lee | 215/251 |
| 5,344,036 | 9/1994 | Stanescu et al. | 215/251 |

*Primary Examiner*—Stephen J. Castellano
*Attorney, Agent, or Firm*—Alan W. Fiedler

[57] ABSTRACT

A combination stopper and shield closure for sealing the open end of an evacuated body fluid collection tube to retain the vacuum therein. The stopper and shield are made by co-injection molding with the stopper being retained within a central aperture in the shield by means of an upper and lower flange or a plurality of plugs extending from the stopper into the shield. The upper flange has a convex surface for directing residue body fluid away from the center of the flange to reduce contamination, a gas-barrier to increase the vacuum seal and prevent contamination, cam followers in the base of the shield to interact with cams on the surface of the tube to facilitate closure twist-off, and flexible tabs around the base of the shield to prevent the tube/closure assembly from being pushed out of a needle holder during body fluid collection.

5 Claims, 9 Drawing Sheets

COMBINATION STOPPER-SHIELD CLOSURE

BACKGROUND OF THE INVENTION

1. Field of the Invention

The present invention relates to a combination stopper and shield closure for body fluid collection tubes and, more particularly, relates to an improved combination stopper and shield closure for an evacuated body fluid collection tube having a minimal cross-section at the point of needle penetration together with increased retention against needle sleeve push-back when the needle is being pushed through the stopper.

2. Background Description

An evacuated blood collection tube is commonly used by a doctor, phlebotomist or nurse to draw a sample of body fluid from a patient in a hospital or doctor's office for diagnostic testing. During the use of such a tube a double-ended needle in a needle holder is inserted in a vein of the patient, and the closed evacuated tube is inserted into the open end of the holder until the needle in the holder pierces the tube's closure. The blood collection tube contains a vacuum that then draws a body fluid sample from the patient into the tube. Therefore, it is important for the closure on the tube to fit securely on the open end of the tube and maintain the vacuum in the tube before, during and after the blood collection procedure.

Current closures for evacuated blood collection tubes include plastic shields containing a rubber stopper, wherein the stopper is thick or has an enlarged head to fit snugly within and remain attached to the shield and a plug portion that fits in the open end of the tube. Retention of the stopper in the shield is important when the shield and stopper are being removed from the open end of the tube so that blood within the tube can be tested. An example of a closure of the type discussed above is found in U.S. Pat. No. 4,967,919 (Earhart), which relates to a blood collection assembly having an enlarged rubber stopper within a cap that are both mounted on an open end of a blood collection tube to seal the tube.

It is also important, of course, for the vacuum in the tube to be sufficient to draw body fluid into the tube, since body fluid must be drawn as quickly as possible to minimize the amount of time a patient has one end of the needle in their body, which can be uncomfortable and cause pain. For example, of the vacuum in the tube is deficient, subsequent removal of the tube from the needle holder and insertion of another tube in the needle holder would be necessary which prolongs the unpleasant procedure. Therefore, it is important that the closure fit within the open end of the tube to retain the vacuum in the tube before, during and sometimes after use.

Currently the design of closures has required a trade-off between the force necessary for inserting a needle through the rubber stopper and into the tube to draw body fluid into the tube and the force needed to withdraw the closure from the tube in the laboratory. Using plastic shields over rubber stoppers has provided a sufficient gripping surface to enable a user to easily remove the stopper from the evacuated tube and overcome the force of the vacuum within the tube. However, rubber stoppers have commonly been so thick that increased force is necessary for the needle to penetrate through the stopper into the tube.

SUMMARY OF THE INVENTION

The present invention overcomes the problems identified in the background material by providing a stopper and shield closure having a reduced thickness and increased retention against needle push-back of the stopper potion, without increasing the force necessary to remove the closure from the tube for testing purposes.

A preferred embodiment of a closure according to the present invention includes a stopper having an upper and lower flange that extends through a central aperture in a shield to securely hold the stopper in the shield. The thickness of the diaphragm between the upper and lower flange is minimized to reduce the force needed to have a needle penetrate the diaphragm, enter the tube and reseal. The closure forms a primary and secondary seal with the tube by having a lip on the stopper extend up the interior wall and over the open end of the tube.

Other embodiments of a closure according to the present invention include additional features, such as, e.g., an annular well in the upper flange for collecting residue body fluid after a needle has been withdrawn from the diaphragm, a curved surface at the base of the well that causes residue body fluid to drain into a trap around the base of the well, cams on the outside surface or end of the tube that interact with cam followers on the shield to facilitate closure twist-off, and flexible tabs around the base of the shield that mate with an interior wall of a needle holder to prevent push-off of the closure from the needle holder that may be caused by the force of a needle sleeve used to seal the needle inside the holder.

These and other aspects, features and advantages of the present invention will become apparent from the following detailed description taken in conjunction with the accompanying drawings.

DETAILED DESCRIPTION

Figure 1:
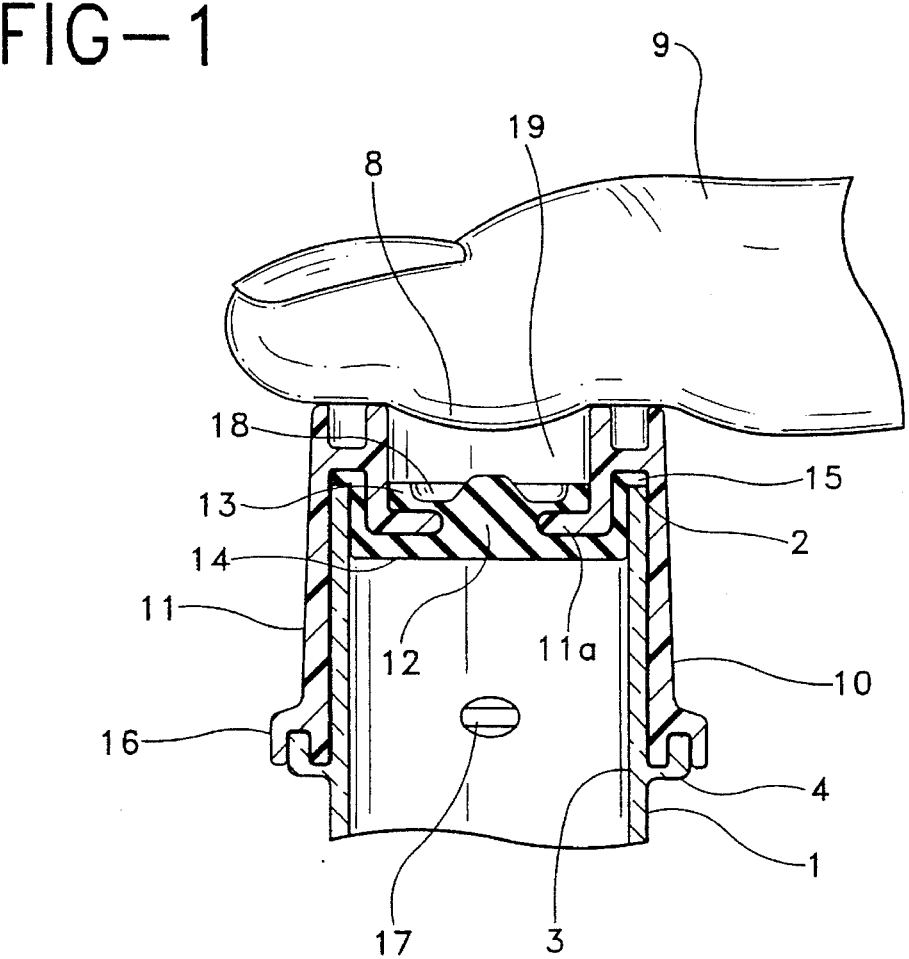
FIG. 1 is a cross-sectional view of a combination stopper and shield closure according to the present invention.

FIG. 1 is a cross-sectional view of a closure 10 according to the present invention mounted on an evacuated collection tube 1. Closure 10 includes a shield 11 and a stopper 12, with stopper 12 having an upper flange portion 13 and a lower flange portion 14 that are positioned on opposite sides of a central aperture 11a in shield 11. Lower flange portion 14 includes a lip 15 that mates with an interior wall 3 and a rim 2 of tube 1 to provide primary and secondary seals between stopper 12 and tube 1. Tube 1 includes an annular cam ring 4 that extends from the exterior of wall 3 and is positioned to receive a cooperating cam follower ring 16 at the base of shield 11. Cam follower ting 16 is received in cam ring 4 on tube 1 to prevent body fluid on wall 3 near rim 2 of tube 1 from flowing down the exterior surface of tube 1 and coming into contact with a user.

FIG. 1 also shows a user's finger 9 over a well 19 at the top of shield 11 with a portion 8 of finger 9 extending into well 19. Well 19 is deep enough so that portion 8 can not come into contact with the surface of upper flange 13. An annular trough 18 in the surface of upper flange 13 ensures that body fluid remaining in well 19 drains into trough 18 to further remove it from portion 8 of patient's finger 9, which alleviates accidental contact by a patient or user with body fluid contained in well 19 of closure 10. In addition, the distance between cam follower ring 16 and lower flange 14 of stopper 12 is large enough that user's finger 9 can not come into contact with the surface of lower flange 14.

Figure 1A:
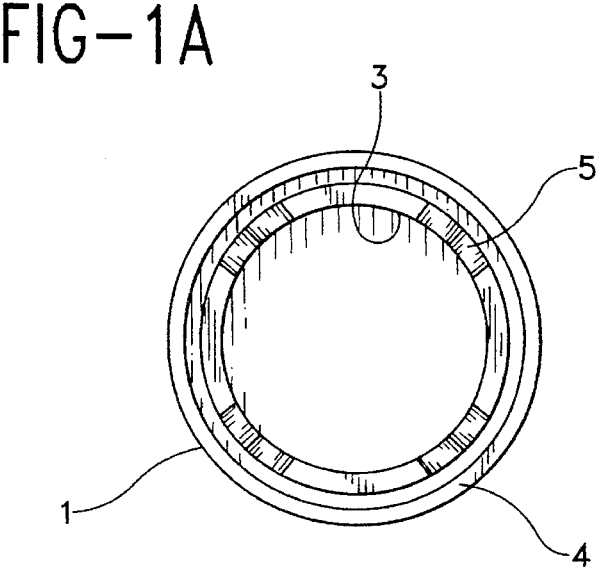
FIG. 1A is a top view of tube 1 shown in FIG. 1.
Figure 1B:
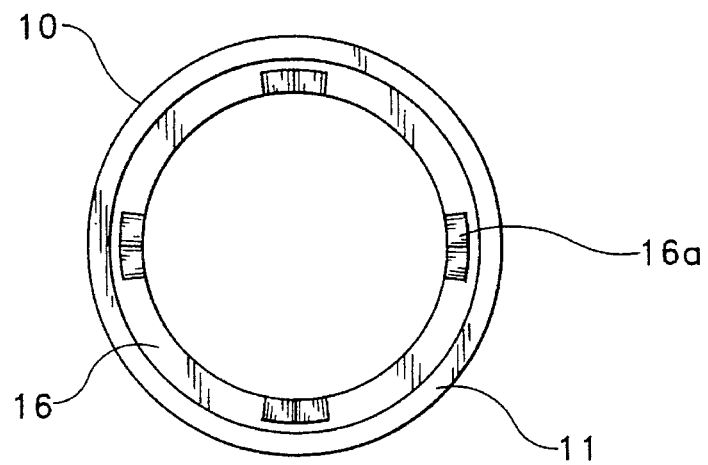
FIG. 1B is a bottom view of closure 10 shown in FIG. 1.

FIG. 1 also shows a projection 17 on the interior surface of shield 11 that mates with the exterior surface or outer wall of tube 1 to securely lock closure 10 onto tube 1. As projection 17 slides over the outer wall an audible snap is generated when rings 4 and 16 mate together to prevent further downward movement of closure 10 on tube 1. As closure 10 is rotated on tube 1, cams 5 in ring 4 on tube 1, shown in FIG. 1A, and cam followers 16a in ring 16 on shield 11, shown in FIG. 1B, interact to facilitate twist-off of closure 10 from tube 1 by releasing projection 17 from the locking ring and opening the primary and secondary seals.

FIGS. 2 through 11 are cross-sectional views of various alternative embodiments of closures that include additional features of the present invention.

Figure 2:
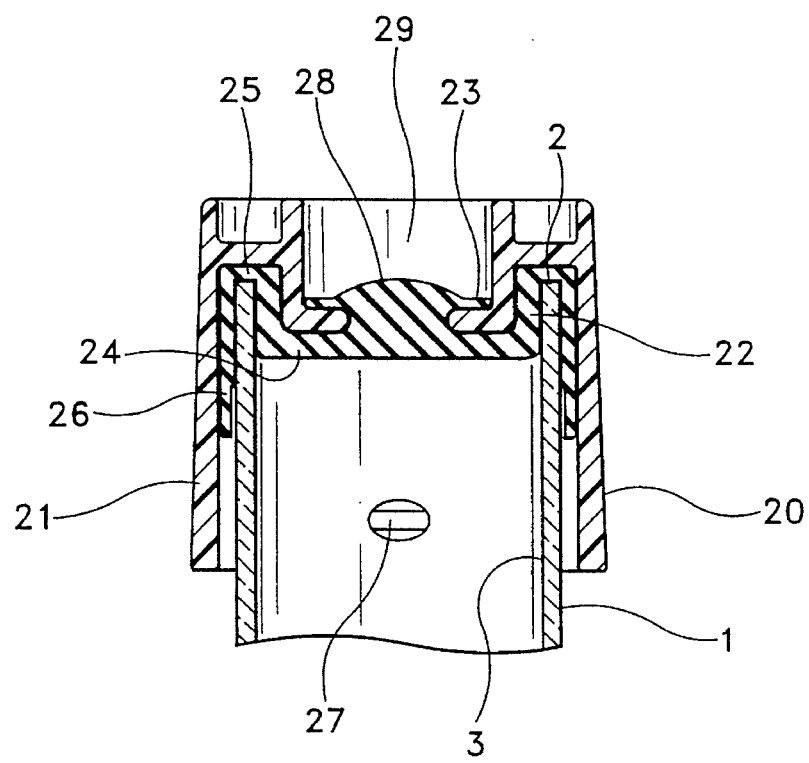
FIGS. 2 through 11 are cross-sectional views of alternative embodiments of a combination stopper and shield closure according to the present invention.

FIG. 2 is a cross-sectional view of a closure 20 having a shield 21 and a stopper 22 that is similar to closure 10, described above, but it includes a modified upper and lower flange 23 and 24, respectively. Upper flange 23 has a convex surface that directs body fluid on the surface towards outer walls of well 29 within shield 21, rather than into a trough like that shown in closure 10. Lower flange 24 includes a vertical extension 26 that extends from a lip 25 at rim 2 of tube 1 down the exterior side of wall 3 of tube 1, which provides a third seal to supplement the primary and secondary seals provided between lip 25, rim 2 and wall 3 in closure 10. Vertical extension 26 also improves the retention force needed to prevent stopper 22 from separating from shield 21 when a needle is pierced through flanges 23 and 24 into tube 3 during collection. Closure 20 also includes projections 27 that are similar in shape and function to projections 17 in closure 10.

Figure 3:
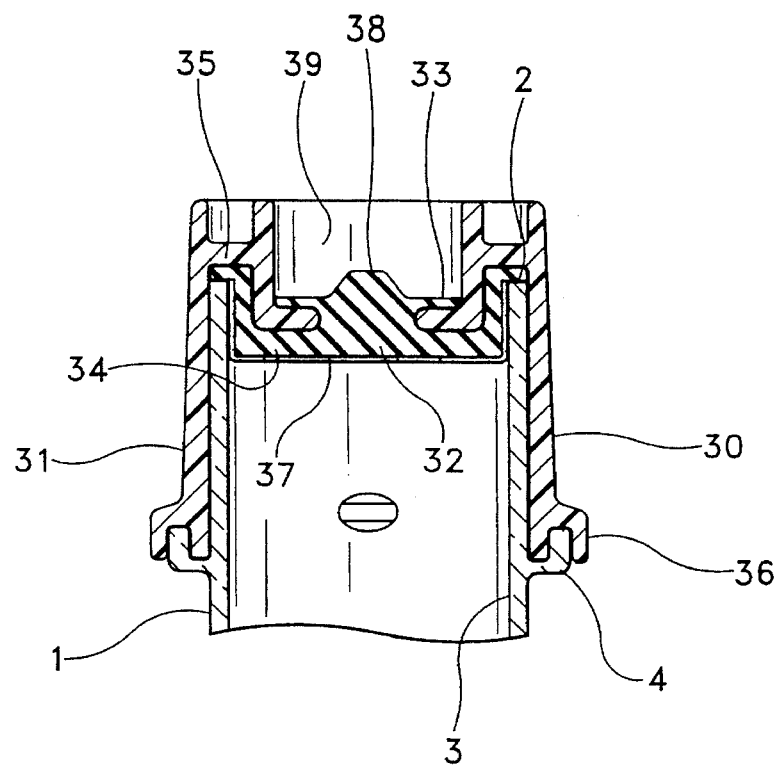

FIG. 3 is a cross-sectional view of an alternative embodiment of a closure 30 according to the present invention that combines the features of closures 10 and 20 discussed above. Closure 30 includes a shield 31 and a stopper 32, wherein stopper 32 has an upper flange 33 and a lower flange 34 with lower flange 34 having a lip 35 that rests on rim 2 of tube 1. Upper flange 33 includes a convex portion 38, similar to the convex surface in closure 20, which lies within well 39 of shield 31 to divert body fluid within well 39 towards the outer wall of well 39. In addition, convex portion 38 is sufficiently spaced from the open end of shield 31 so that a user's finger will not come into contact with body fluid within well 39. Closure 30 also includes a cam follower ring 36 on shield 31 that mates with a cam ring 4 on tube 1. Cams 5 in ring 4 permit closure 30 to be twisted off tube 1 via the cam action between cams 5 in ring 4 and cam followers (not shown) in ring 36 during closure rotation. FIG. 3 also includes a gas-barrier member 37 comprised of a laminated metallic or resin film on the bottom surface of stopper 32 which improves vacuum retention between closure 30 and tube 1.

Figure 4:
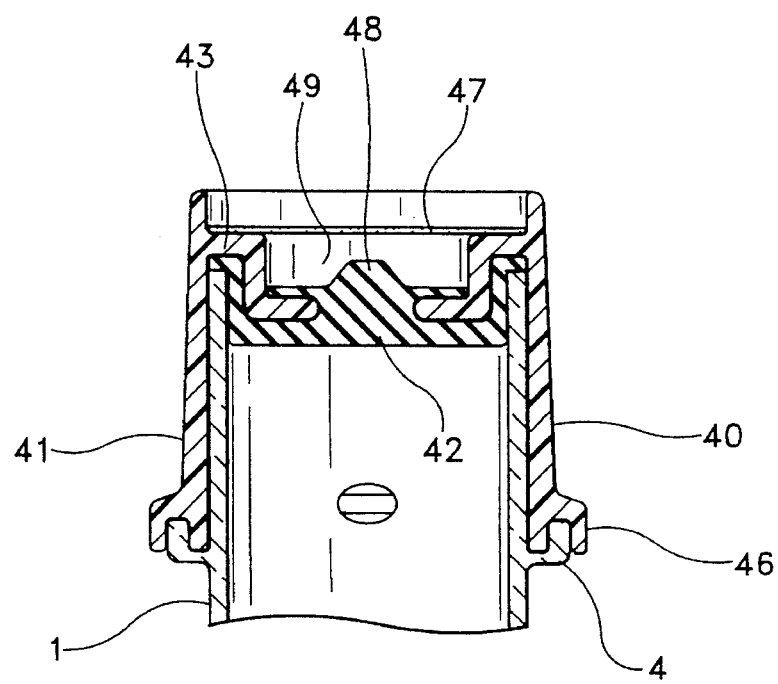

FIG. 4 shows a closure 40 substantially similar to closure 30 shown in FIG. 3, however, a gas-barrier member 47 of a laminated metallic or resin film is bonded to a rim 43 on shield 41 and extends over the entrance to upper well 49. Gas-barrier member 47, therefore, provides a cover for the body fluid trap surrounding a convex portion 48 and also prevents contamination that could be caused by the finger of a user. The remainder of closure 40 is substantially similar to closures 10 and 30 described above, including projections like projections 17 and 27 in FIGS. 1 and 2, respectively, and a lower cam follower ting 46 on shield 41 that engages with a cam ring 4 on an external surface of tube 1 to provide the twist-off closure feature. In addition, stopper 42 is substantially similar to stopper 32 shown and described in FIG. 3, having a similar lower flange with a lip and a similar upper flange with a convex portion 48 so that residue body fluid left from a needle being withdrawn from stopper 42 will flow to the outer wall of well 49. This feature is important since it prevents body fluid from collecting where the needle penetrated stopper 42, which minimizes the possibility of contaminating instrument probes used to draw body fluid out of tube 1 through stopper 42.

Closures 10, 20, 30 and 40 are manufactured using co-injected molding, with the shield being made of plastic and the stopper being made of a rubber or thermoplastic elastomer in a single process. In addition, as discussed above, each of these closures has a primary seal around an internal diameter of tube 1 and a secondary seal around the rim of tube 1 to retain a vacuum within tube 1. However, closure 20 in FIG. 2 also provides a third seal around the outer diameter of tube 1 to further retain the vacuum.

Figure 5:
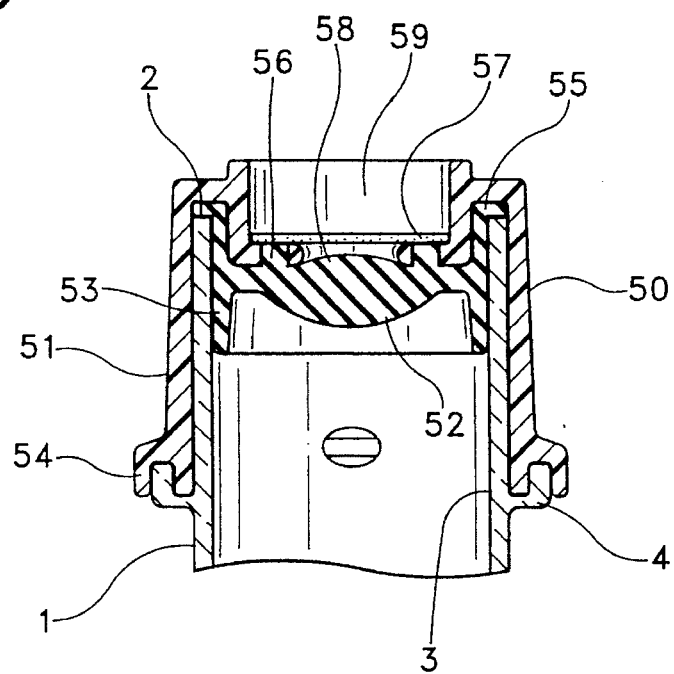

FIG. 5 is a cross-sectional view of a closure 50 having a shield 51 with an internal sealing element 52 fastened to shield 51 by a plurality of plugs 56 extending into a well 59 in shield 51. Sealing element 52 also includes an arm 55 that extends up the internal surface of wall 3 on tube 1 and over a rim 2 and a lower extension 53 that extends down the inner surface of wall 3. The interaction between extension 53, arm 55 and wall 3 provide primary and secondary seals between sealing element 52 and tube 1. Shield 51 also includes a cam follower ring 54 that mates with cam ring 4 on tube 1 to provide a twist-off release for closure 50 from tube, when closure 50 is rotated either counterclockwise or clockwise.

Closure 50 in FIG. 5 has a gas-barrier member 57 made of a laminated metallic or resin film bonded across the bottom of well 59 to provide an improved vacuum retention capability and sealing element 52 includes a convex portion 58 at the base of well 59 so that residue body fluid from a needle being retracted from sealing element 52 flows to the wall of well 59. Both of these features also protect sealing element 52 from contamination from user's fingers and prevent body fluid from contaminating instrument probes being used to draw body fluid from tube 1 through sealing element 52.

Figure 6:
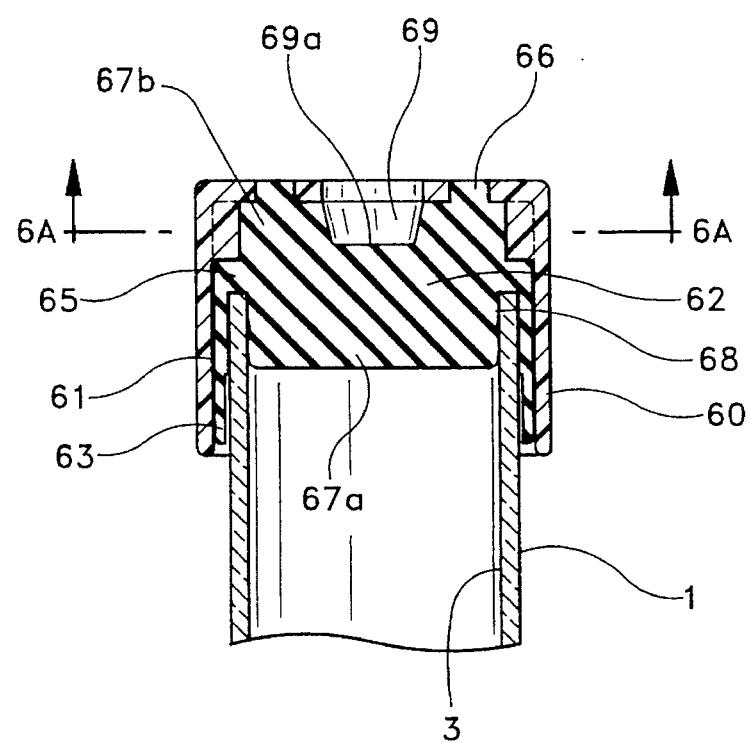
Figure 6A:
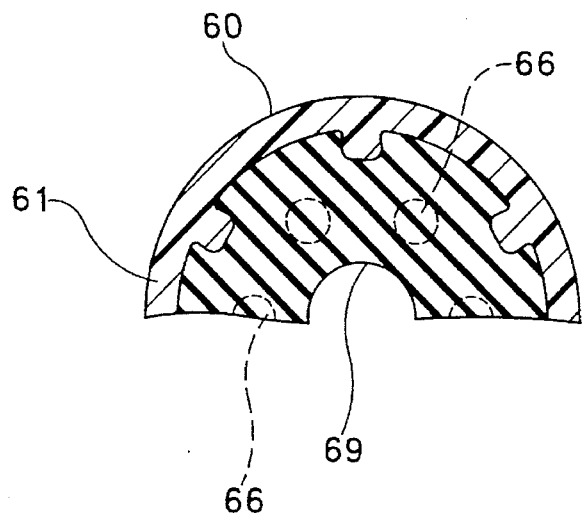
Figure 7:
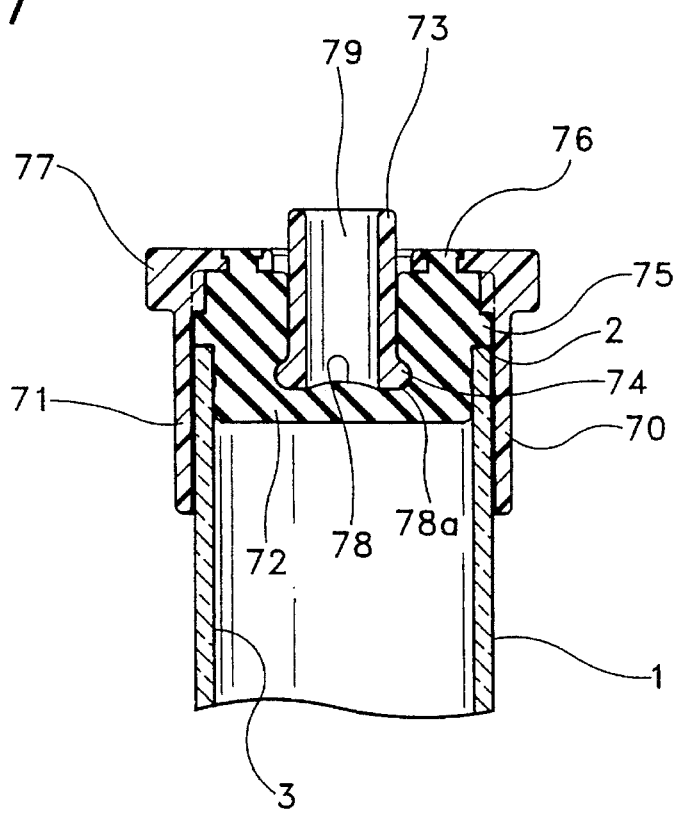
Figure 8:
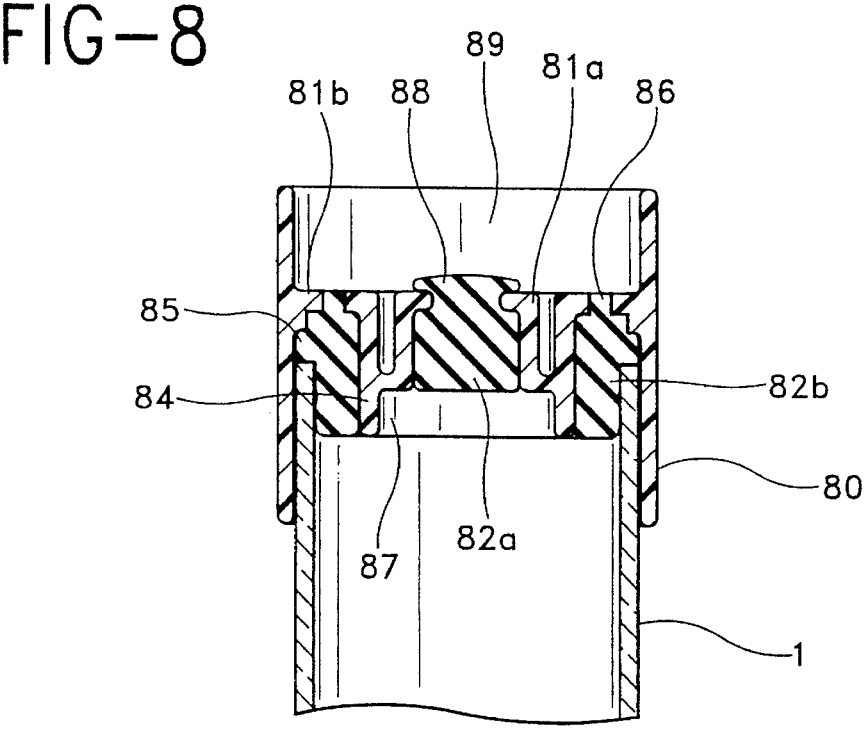

FIGS. 6, 7 and 8 show various other embodiments of closures according to the present invention. Each of these closures 60, 70 and 80 have an increased volume of rubber in their sealing elements to improve gas-barrier protection, since thin sections of injected molded sealing elements tend to be porous.

FIG. 6 is a cross-sectional view of closure 60 having a shield 61 and a sealing element 62 including a lower portion 67a and an upper portion 67b. Upper portion 67b includes a plurality of annular protrusions 66 extending into sealing element 62 to hold sealing element 62 within shield 61, and lower portion 67a includes a plurality of annular tings 68 that engage the internal diameter of tube 1 to provide a primary vacuum seal on tube 1. Sealing element 62 also includes an extension 63 that extends from an arm 65 to provide a secondary seal around the outer diameter of tube 1. By using annular protrusions 66, the internal stresses on sealing element 62 are significantly less than those created on sealing elements secured to a shield using an interference fit, i.e., compression of the sealing element body within a shield. Creep-out of sealing element 62 from shield 61, after the needle has been removed from sealing element 62 is also reduced.

Closure 60 also has a sufficiently deep well 69 with a convex shape 69a at its bottom so that body fluid in well 69 can not be touched by a user's finger and will drain towards the wall of well 69 to prevent contamination of a body fluid sampling instrument probe that is being inserted into sealing element 52 that has been penetrated.

FIG. 7 is a cross-sectional view of a closure 70 having a shield 71, a sealing element 72 and a hollow shaft 73. Closure 70 is designed for easy insertion into and removal from tube 1 by the user applying downward pressure on shaft 73 and pressure in the opposite direction on a top flange 77 of shield 71. As pressure is applied to shaft 73, sealing element 72 is stretched downward, which causes the lower section walls of sealing element 72 to release from the internal surface of wall 3 on tube 1. Sealing element 72 is mounted to shield 71 by a plurality of plugs 76 that extend into flange 77 of shield 71 and includes an arm 75 that contacts rim 2 of tube 1 to provide a primary seal. Arm 75 also extends into the wall of shield 71 to retain sealing element 72 in shield 71.

Hollow shaft 73 also forms a well 79 in the top of closure 70 with the base of well 79 having a convex portion 78 to direct body fluid away from the center of well 79 towards the wall of shaft 73. Shaft 73 includes an expanded lip 74 that mates with a groove 78a surrounding convex portion 78 at the base of well 79 to retain shaft 73 within sealing element 72.

FIG. 8 is a cross-sectional view of a closure 80 having a shield 81 and a sealing element 82. A center portion 82a of sealing element 82 is secured to an axial collar 81a, and a ting portion 82b of sealing element 82 is secured by a plurality of plugs 86 to a recessed rim 81b. Ring portion 82b of sealing element 82 includes an arm 85 that (1) extends over rim 2 of tube 1 when closure 80 is attached to tube 1 to seal tube 1 and (2) extends into the side of shield 81 to securely hold sealing element 82 within shield 81. Center portion 82a of sealing element 82 includes a convex-shaped portion 88 into which a needle is inserted to enter tube 1, with convex portion 88 being shaped so that residue body fluid on portion 88 flows away from the center of portion 88 into a trap at the base of well 89. Axial collar 81a of shield 81 includes a lower extending portion 84 that forms a lower well 87 in shield 81 and provides support for ring portion 82b of sealing element 82 where it is in contact with and seals the internal diameter of tube 1. Since portions 82a and 82b of sealing element 82 have less internal stress than would be the case of an interference fit was used, the possibility of creep-out after needle penetration is decreased.

Figure 9:
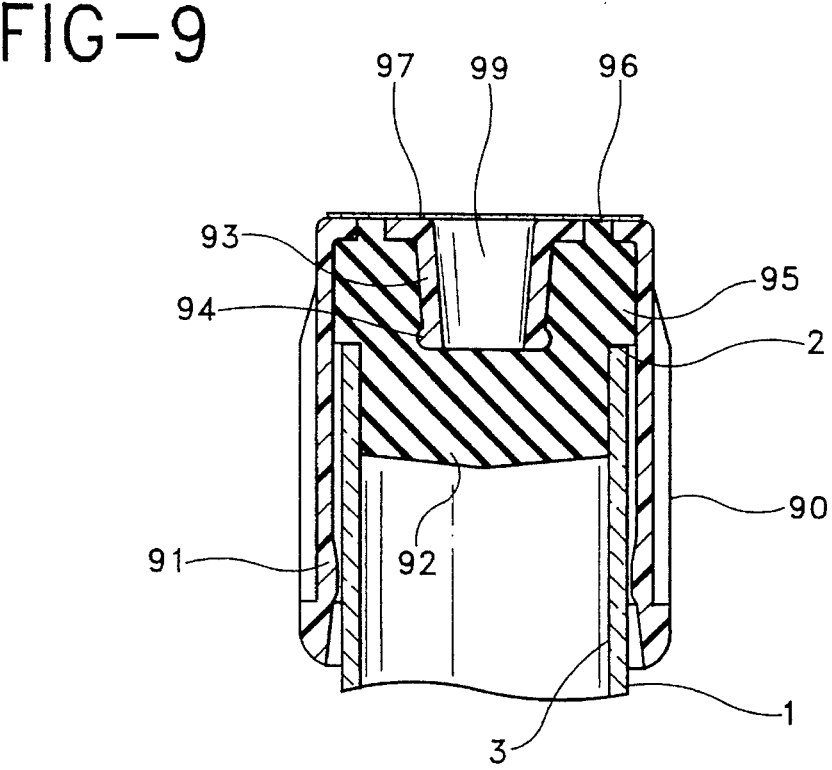
Figure 10:
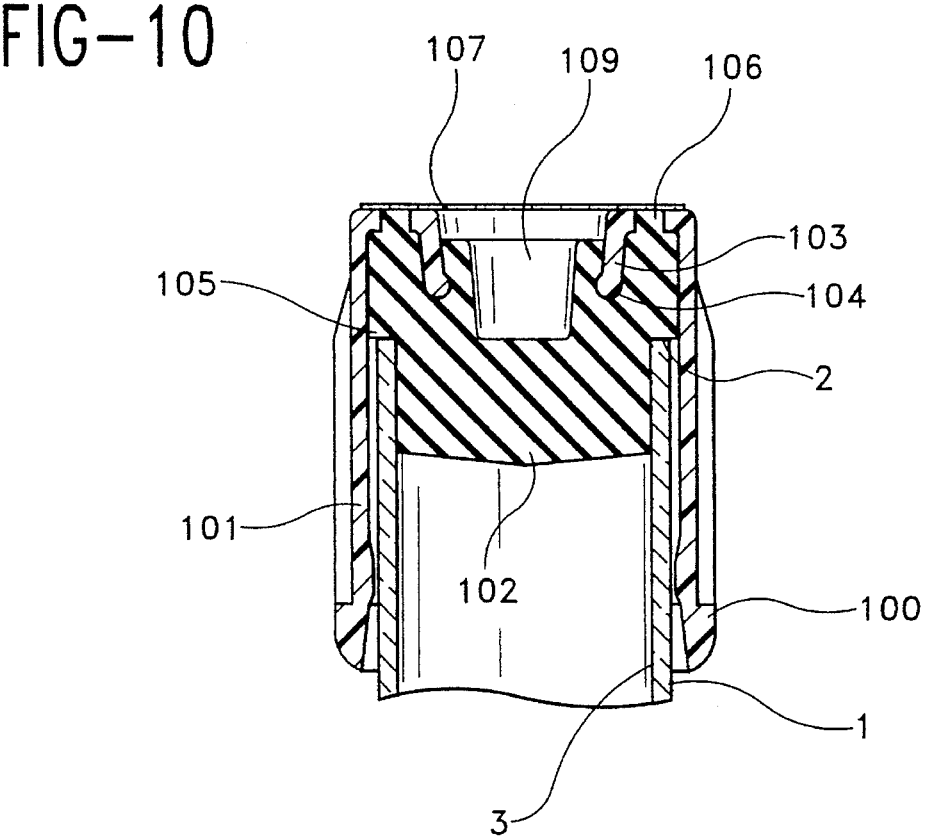

FIGS. 9 and 10 show cross-sectional views of closures 90 and 100, respectively, that have a larger mass of rubber within sealing elements 92 and 102, respectively, to provide increased gas-barrier protection. In addition, closures 90 and 100 include gas-barrier members 97 and 107, respectively, made of a metallic or resin film bonded to the upper surface of each closure to provide additional gas-barrier protection.

In closure 90 in FIG. 9, shield 91 is attached to sealing element 92 by a plurality of plugs 96 and includes a hollow shaft 93 having an expanded lip 94 that extends into and locks to the bottom of a well 99. Lip 94 mates with the internal surface of well 99 to hold sealing element 92 within shield 91 during needle penetration and removal of closure 90 from tube 1. An arm 95 extends over rim 2 of tube 1 to provide a primary seal and a lower portion of sealing element 92 provides a secondary seal with the inner surface of wall 3 of tube 1.

Closure 100 in FIG. 10 is similar to closure 90, however, sealing element 102 is secured to shield 101 by an axial collar 103 that is located outside of a well 109. Axial collar 103 on shield 101 is locked to sealing element 102 by an expanded lip 104 at the base of axial collar 103 within sealing element 102. A plurality of protrusions 106 are also used to secure sealing element 102 to shield 101 and a gas-barrier member 107 extends across the top of closure 100 to provide gas-barrier protection and protect body fluid well 109 from contamination by a user's finger.

Closures 90 and 100 both have a convex shape at the bottom of their respective wells 99 and 109 to trap body fluid that remains in the well when a needle is withdrawn from each respective sealing element. As discussed above, this feature is important since it reduces the possibility of contamination of a body fluid sampling instrument that is used to withdraw body fluid from tube 1. In addition, since a plurality of plugs 96 and 106 are used to retain each sealing element within the shield, the internal stresses on the sealing elements are significantly less than those created by interference fit, which reduces needle penetration force.

Figure 11:
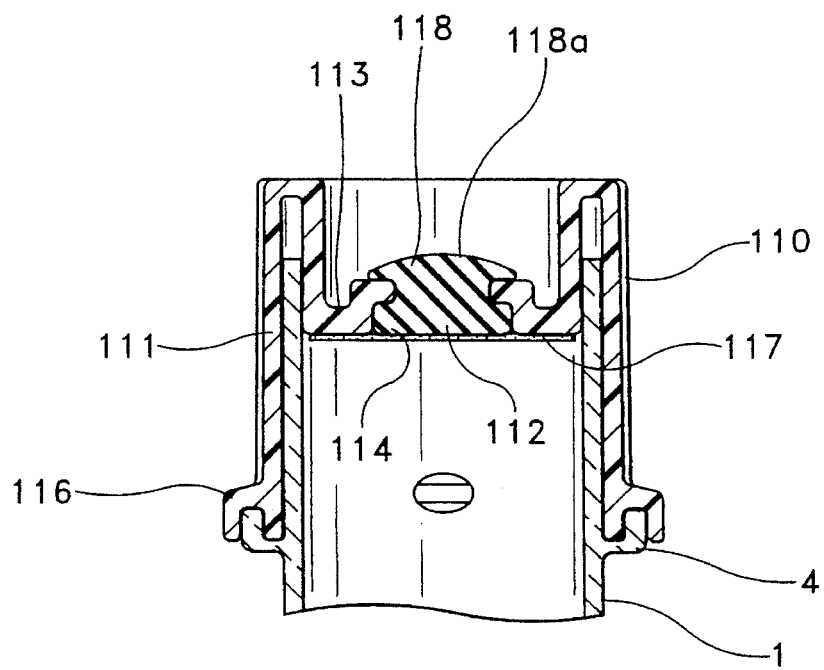

FIG. 11 is a cross-sectional view of an alternative embodiment of a closure 110 according to present invention including a shield 111 and a sealing element 112. Sealing element 112 has a convex portion 118a that directs body fluid away from the center of sealing element 112 towards a body fluid trap 113 surrounding convex portion 118a. Sealing element 112 also includes a lower flange 114, that in combination with an upper portion 118, securely holds sealing element 112 within shield 111. A gas-barrier member 117 made of a laminated metallic or resin film is bonded across the bottom of lower flange 114 to provide improved vacuum retention for tube 1. Closure 110 also includes a cam follower ring 116 that mates with a cam ring 4 extending from the side of tube 1 to aid in removing closure 110 from tube 1 when closure 110 is rotated.

Figure 12:
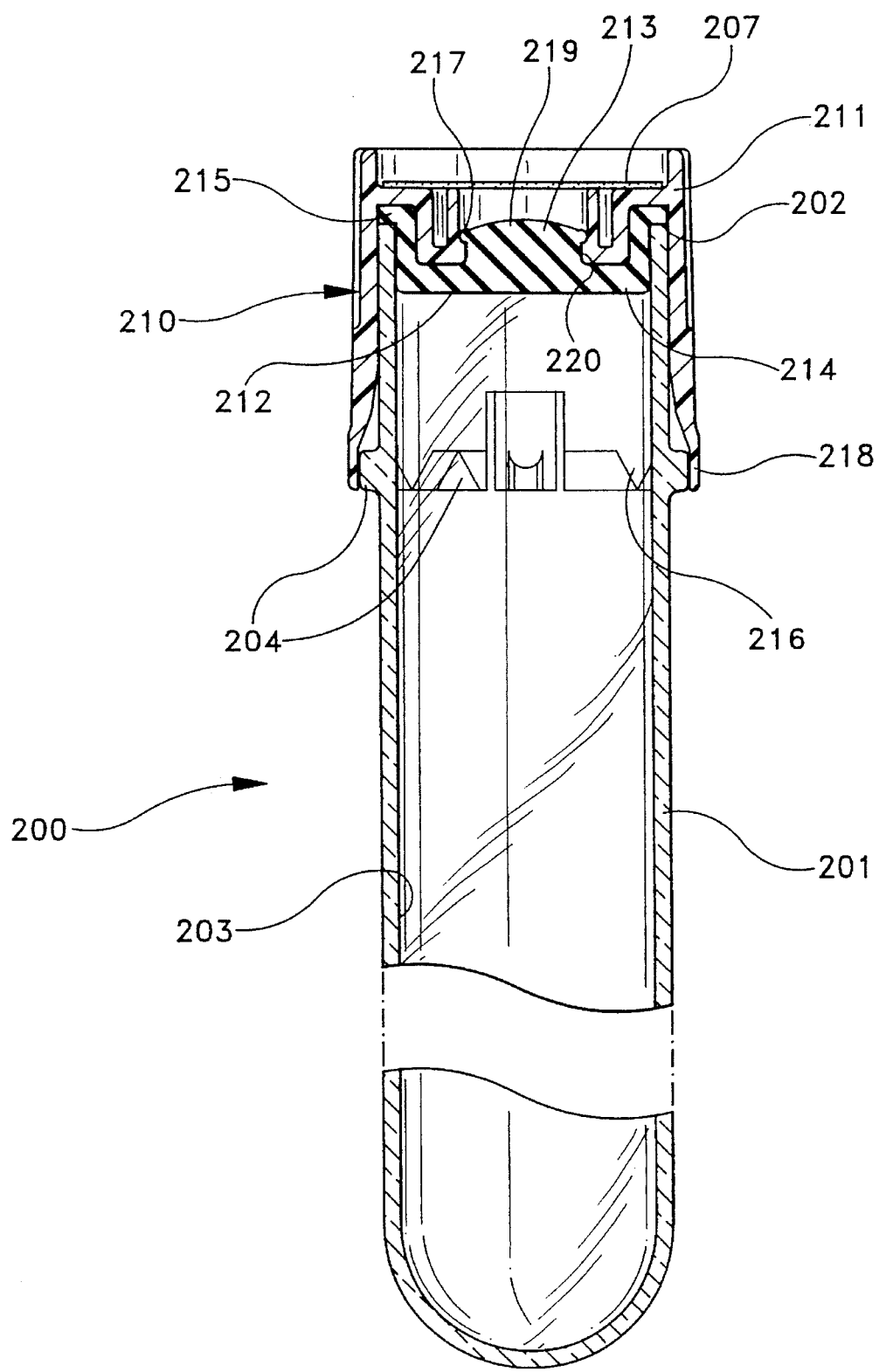
FIG. 12 is a cross-sectional view of an assembly including an alternative embodiment of a combination stopper and shield closure according to the present invention mounted on an evacuated blood collection tube.
Figure 13:
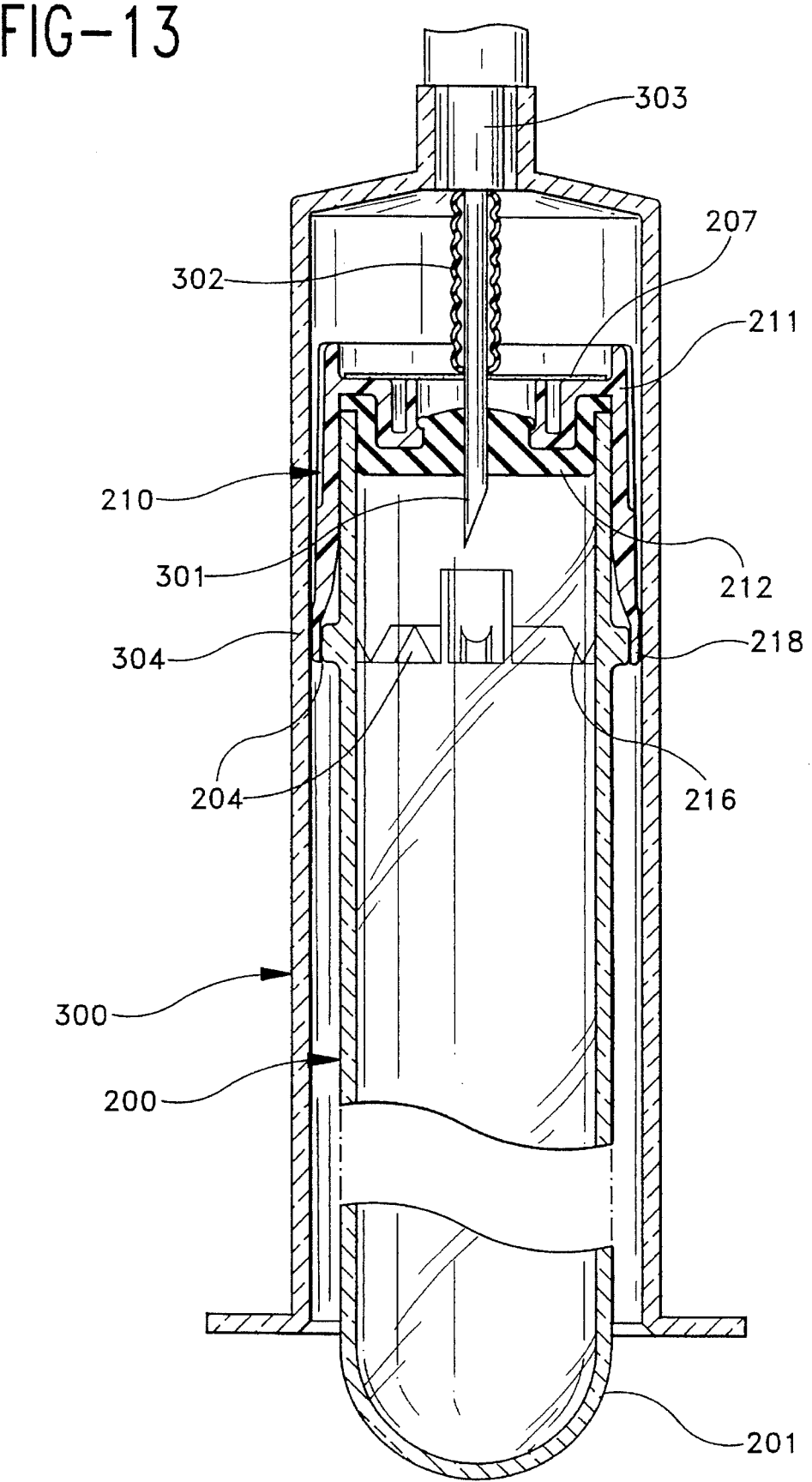
FIG. 13 is a cross-sectional view of the assembly shown in FIG. 12 mounted in a needle holder during blood collection.

FIGS. 12 and 13 relate to an alternative embodiment of a combination stopper and shield closure 210 of the present invention that includes a special holder retaining means that securely holds assembly 200 within a needle holder 300 and prevents push-back that may be caused by a collapsible needle sleeve 302 in holder 300.

FIG. 12 is a cross-sectional view of an assembly 200 including an alternative embodiment closure 210 having a stopper 212 and shield 211 according to the present invention shown mounted on a evacuated blood collection tube 201. Stopper 212 includes an upper flange portion 213 and a lower flange portion 214 that are positioned on opposite sides of a central aperture 220 in shield 211. Upper flange portion 213 includes a bead 217 that extends beyond the edge of aperture 220 to secure stopper 212 within shield 211 during needle penetration and has a convex surface 219 that directs residue body fluid away from the center of surface 219 towards bead 217 to prevent body fluid from collecting where a needle has penetrated stopper 212 and minimize the possibility of contaminating instrument probes used to draw body fluid out of tube 201. Lower flange portion 214 includes a lip 215 that extends up an interior wall 203 and over a rim 202 of tube 201 to provide a seal between stopper 212 and tube 201. A gas-barrier member 207 made of a laminated metallic or resin film is also bonded across the top of closure 210 to provide a seal for improved vacuum retention in tube 201 and protect stopper 212 from contamination from a user's fingers.

Tube 201 in FIG. 12 includes a plurality of cams 204 that extend from the exterior of wall 203 and are positioned to be received within the base of shield 211, and shield 211 includes a plurality of cam followers 216 around its base. Cam followers 216 interact with cams 204 on tube 201 to facilitate twist-off of closure 210 from tube 201 when closure 210 is rotated on tube 201.

Shield 211 also includes a plurality of flexible tabs 218 that extend out from the base of shield 211 and away from wall 203 of tube 201 when closure 210 is mounted on tube 201. However, when assembly 200 is mounted within a needle holder 300 during blood collection, as shown in FIG. 13, flexible tabs 2118 are compressed inwardly towards wall 203 of robe 201 by force from a wall 304 of holder 300. The interaction between tabs 218 and wall 304 retain assembly 200 within needle holder 300 and prevent assembly 200 from being pushed out of holder 300 by pressure from collapsible needle sleeve 302, described below.

Needle holder 300 shown in FIG. 13, basically includes a double-ended needle 301 with one end of needle 301 extending into a distal end 303 of holder 300 and covered by collapsible needle sleeve 302 that seals the end of needle 301 to prevent body fluid from flowing from needle 301 into holder 300. As assembly 200 is inserted into holder 300, needle 301 pierces gas-barrier member 207 and stopper 212 to enter tube 201 and permit the vacuum within tube 201 to draw body fluid from a patient through needle 301 into tube 201. As needle 301 penetrates member 207 and stopper 212, needle sleeve 302 is collapsed to open the end of needle 301 but then causes pressure to be applied in the opposite direction against assembly 200. However, interaction between tabs 218 on closure 210 and wall 304 of holder 300 retain assembly 200 in position and prevent assembly 200 from being pushed out of holder 300. When body fluid collection with assembly 200 is complete, assembly 200 is removed from holder 300 and needle sleeve 302 again expands and seals the end of needle 301 to prevent body fluid from flowing through needle 301 into holder 300, until another assembly 200 has been inserted in holder 300.

All of the above-described closures are manufactured using co-injection molding wherein the sealing element and the shield are manufactured together. The shield is made of a harder plastic than the material used to make the sealing element, so that the sealing element can properly seal the open end of the tube and retain the vacuum within the tube, but still soft enough to be pierced by a needle. For example, the sealing element or stopper is made of a thermoplastic elastomer material. However, of course, these manufacturing techniques and materials are merely exemplary, various other manufacturing methods and materials could also be used.

In the foregoing discussion, it is to be understood that the above-described embodiments of the present invention are simply illustrative of various features that can be used in closures to be used to seal evacuated body fluid collection tubes. Other suitable variations, modifications and combinations of these features could be made to or used in these embodiments and still remain within the scope of the present invention.

What is claimed is:

1. A closure for sealing an open end of a body fluid collection tube comprising:

a shield having a wall;

a stopper for sealing the tube that is received in said shield and includes a top surface, wherein said top surface of said stopper in conjunction with said wall of said shield form a well, and said top surface includes a convex portion that directs residue body fluid from said convex portion towards said wall; and a gas-barrier member bonded to said shield to improve vacuum retention within the tube and protect said well from contamination.

2. A closure according to claim 1, wherein said stopper further comprises a body fluid trap surrounding said convex portion that collects the residue body fluid being directed from said convex portion towards said wall.

3. A closure according to claim 1, wherein said shield further comprises an outer skirt having a plurality of projections extending from an interior surface of said outer skirt into said shield, said projections on said outer skirt positioned to mate with an outer wall of the tube to securely lock said closure onto the tube and retain the vacuum within the tube.

4. A closure according to claim 3, wherein said shield further comprises a cam follower ring around said outer skirt that interacts with a cam ring on the outer wall of the tube to facilitate unlocking and removal of said closure from the tube when said closure is rotated on the open end of said tube.

5. A closure according to claim 1, wherein said stopper further comprises a lower flange with a lip that forms a primary seal with an inside wall and a rim at the open end of the tube to minimize the thickness of said stopper and reduce needle penetration force through said stopper.

* * * * *